US00PP08629P

United States Patent [19]

Zary

[11] Patent Number: Plant 8,629

[45] Date of Patent: Mar. 8, 1994

[54] HYBRID TEA ROSE PLANT NAMED 'JACMER'

[75] Inventor: Keith W. Zary, Thousand Oaks, Calif.

[73] Assignee: Bear Creek Gardens, Inc., Medford, Oreg.

[21] Appl. No.: 991,631

[22] Filed: Dec. 15, 1992

[51] Int. Cl.[5] ..... A01H 5/00

[52] U.S. Cl. ..... Plt./17

[58] Field of Search ..... Plt. 11, 16, 17, 20

*Primary Examiner*—Howard J. Locker

*Attorney, Agent, or Firm*—Klarquist, Sparkman, Campbell, Leigh and Whinston

[57] ABSTRACT

A Hybrid tea class rose plant having a high production of cut-flower stems, good vase life, small thorns and novel flower color.

1 Drawing Sheet

1

The present invention relates to a new and distinct variety of rose plant of the Hybrid tea class which was originated by me by crossing an unnamed seedling with the variety anKORi, U.S. Plant Pat. No. 5,012.

The primary objective of this breeding was to produce a new rose variety having the orange hybrid tea flower of the female unnamed seedling combined with the vigor and upright growth of the variety anKORi. The objective was substantially achieved along with other desirable improvements as evidenced by the following unique combination of characteristics which are outstanding in the new variety and which distinguish it from its parents, as well as from all other varieties of which I am aware:

1. Novel flower color;
2. High cut-flower production, average production being 34 stems per plant in one year;
3. Good vase life;
4. Small thorns.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—anKORi, U.S. Plant Pat. No. 5,012.

Classification:

*Botanical.*—Rosa hybrida.

*Commercial.*—Hybrid tea.

FLOWER

Observations made from specimens grown in a greenhouse environment in Somis, Calif., from January through June, 1992.

2

Blooming habit: Recurrent.

Bud:

*Size.*—1¼" when the petals start to unfurl.

*Form.*—Short, pointed ovoid.

*Color.*—When sepals first divide, bud color is Red Group 43B. When half blown, the upper sides of the petals are Red Group 40B; and the lower sides of the petals are similar in color but dull.

*Sepals.*—Color: Green Group 138B. Surface texture: Covered with fine hairs. There are three normally appendaged sepals. There are two unappendaged sepals with hairy edges.

*Receptacle.*—Color: Green Group 143B. Shape: Funnel. Size: Broad, ¼"×3/16". Surface: Smooth.

*Peduncle.*—Length: Medium, 3½" to 4". Surface: Prickly. Color: Medium green with some bronzy areas. Strength: Stiff, erect.

Bloom:

*Size.*—Medium. Average open size is 3½" to 4".

*Borne.*—Singly.

*Stems.*—Medium, strong, average, 20" to 22".

*Form.*—When first open: high centered. Permanence: Retains its form to the end, outer petals curl back in a quill fashion.

*Petalage.*—Number of petals under normal conditions: 30.

*Color.*—The upper side of the petals is Red Group 40B. The reverse side of the petals is similar in color but dull. The bases of the petals have a distinctive yellow half moon at the point of attachment to receptacle. The major color on the upper side is Red Group 40B.

*Variegations.*—None.

*Discoloration.*—The general tonality at the end of the first day: None. At the end of the third day: None.

*Fragrance.*—Slight.

Petals:

*Texture.*—Thick, leathery.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: Long, 7 days. As a cut flower: long, 9 days.

Reproductive parts:

*Anthers.*—Size: Large. Quantity: Many. Color: Yellow. Arrangement: Regular around styles.

*Filaments.*—Color: Yellow.

*Pollen.*—Color: Lemon yellow.

*Styles.*—Color: Red-purple.

*Stigmas.*—Color: Greenish white.

Form: Bush.

Growth: Vigorous, upright and branching.

Foliage: Number of leaflets on normal mid-stem leaves: 5 to 7.

*Size.*—Large, $6\frac{1}{2}'' \times 4\frac{1}{2}''$.

*Quantity.*—Abundant.

*Color.*—New foliage: Bronze. Old foliage: Dark green.

Leaflets:

*Shape.*—Broadly oval.

*Texture.*—Upper side: Smooth.

*Edge.*—Serrated.

*Serration.*—Single, small.

*Petiole rachis.*—Color: Reddish.

*Petiole underside.*—Rough, with prickles.

*Stipules.*—Long, $\frac{3}{4}''$.

*Disease resistance.*—Susceptible to mildew under normal growing conditions in a greenhouse at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Short, less than $\frac{1}{4}''$, straight to hooked slightly downward.

*Color when young.*—Red.

Small prickles:

*Quantity.*—On main stalks: None. On laterals: None.

I claim:

1. A new and distinct variety of rose plant of the Hybrid tea class, substantially as herein shown and described, characterized particularly as to novelty by the unique combination of its high production of cut-flower stems, its good vase life, its small thorns and its novel flower color.

* * * * *

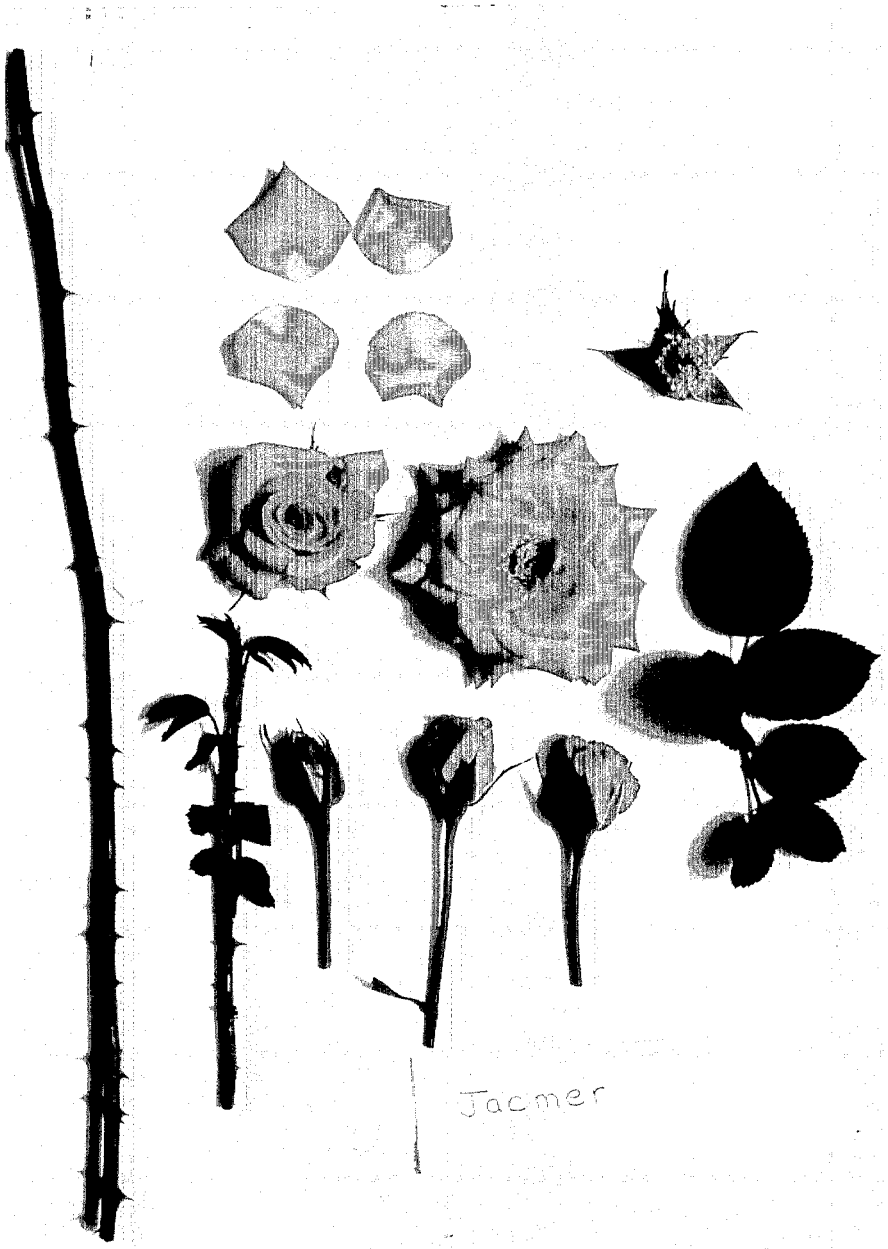
Jacmer